(12) United States Patent
Borca et al.

(10) Patent No.: US 8,846,055 B2
(45) Date of Patent: Sep. 30, 2014

(54) VIRULENCE DETERMINANT WITHIN THE E2 STRUCTURAL GLYCOPROTEIN OF CLASSICAL SWINE FEVER VIRUS

(75) Inventors: Manuel V. Borca, Westbrook, CT (US); Guillermo R. Risatti, Westbrook, CT (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 1303 days.

(21) Appl. No.: 11/443,132

(22) Filed: May 30, 2006

(65) Prior Publication Data

US 2007/0280955 A1 Dec. 6, 2007

(51) Int. Cl.
| | |
|---|---|
| A61K 39/21 | (2006.01) |
| A61K 39/12 | (2006.01) |
| C12Q 1/70 | (2006.01) |
| C07K 14/005 | (2006.01) |
| C12N 7/00 | (2006.01) |
| A61K 39/00 | (2006.01) |

(52) U.S. Cl.
CPC ....... *A61K 39/12* (2013.01); *C12N 2770/24322* (2013.01); *A61K 2039/5254* (2013.01); *C07K 14/005* (2013.01); *C12N 7/00* (2013.01); *C12N 2770/24361* (2013.01)
USPC .......... 424/204.1; 424/205.1; 435/5

(58) Field of Classification Search
USPC ........................................................ 424/402
See application file for complete search history.

(56) References Cited

FOREIGN PATENT DOCUMENTS

NL          EP0982402 A1 *  3/2000  ............. C12N 15/40

OTHER PUBLICATIONS van Gennip et al. Vaccine, 2002, vol. 20, pp. 1544-1556.*
Lin et al. Journal of Virology, 2000, vol. 74, No. 24, p. 11619-11625.*
Risatti et al. Journal of Virology, Mar. 2005, vol. 79, No. 6, p. 3787-3796.*
Gennip et al., Experimental non-transmissible marker vaccines for classical swine fever (CSF) by trans-complementation of E(rns) or E2 of CSFV, 2002, Vaccine, 20:1544-1556.*
van Gennip et al., Chimeric classical swine fever viruses containing envelope protein E(RNS) or E2 of bovine viral diarrhoea virus protect pigs against challenge with CSFV and induce a distinguishable antibody response, 2001, Vaccine, 19:447-459.*

* cited by examiner

*Primary Examiner* — Zachariah Lucas
*Assistant Examiner* — Barry A Chestnut
(74) *Attorney, Agent, or Firm* — John D. Fado; Evelyn M. Rabin (57) ABSTRACT

Classical Swine Fever Virus (CSFV) E2 glycoprotein is a major inducer of neutralizing antibodies and protective immunity in swine. E2 mediates virus adsorption to the target cell, and harbors genetic determinants associated with virus virulence. CSFV E2 also contains between residues 829 and 837 a discrete epitope (TAVSPTTLR) recognized by monoclonal antibody (mAb) WH303, used to differentiate CSFV from related Pestiviruses Bovine Viral Diarrhea Virus (BVDV) and Border Disease Virus (BDV). In this report, a CSFV infectious clone of the virulent Brescia isolate (BICv) was used to progressively mutate the mAb WH303 epitope of CSFV E2 to the homologous amino acid sequence of BVDV strain NADL E2 (TSFNMDTLA). While the resulting virus mutants T1v (TSFSPTTLR), T2v (TSFNPTTLR), T3v (TSFNMTTLR) demonstrated in vitro growth characteristics similar to those of parental BICv, mutants T4v (TSFNMDTLR) and T5v (TSFNMDTLA) exhibited a 10-fold decrease in virus yield and a significant decrease in plaque size relative to parental BICv. Immunohistochemical reactivity with WH303 was lost only in T3v, T4v and T5v. Interestingly, progressive mutation of the WH303 epitope had an additive effect on attenuation for the virus in swine, with mutants T1v, T2v or T3v inducing progressively milder but invariably lethal CSF, T4v inducing only mild and transient clinical disease, and T5v inducing no disease. Swine infected with either T4v or T5v showed decreased virus replication in tonsils, draining lymph node, spleen and kidney and a significant reduction in virus shedding. Finally, T5v-infected animals were protected from clinical disease when challenged with virulent Brescia virus at 3 or 21 days post T5v inoculation. These results indicate that amino acid residues 830 to 834 of E2 are critical for virulence of CSFV in swine and that engineering at this locus may provide basis for a rationally designed live attenuated CSF vaccine.

7 Claims, 7 Drawing Sheets

|  | 829 ←--- CSFV residue ---→ 837 |
|---|---|
| Brescia | T  A  V  S  P  T  T  L  R |
| BVDV | T  *S  F  N  M  D*  T  L  *A* |
|  |  |
| T1v | T  *S  F*  S  P  T  T  L  R |
| T2v | T  *S  F  N*  P  T  T  L  R |
| T3v | T  *S  F  N  M*  T  T  L  R |
| T4v | T  *S  F  N  M  D*  T  L  R |
| T5v | T  *S  F  N  M  D*  T  L  *A* |

Fig. 6

SEQUENCE LISTING

<160> NUMBER OF SEQ ID NOS: 12

<210> SEQ ID NO 1
<211> LENGTH: 9
<212> TYPE: PRT
<213> ORGANISM: Unknown
<220> FEATURE:
<223> OTHER INFORMATION: Chemically Synthesized

<400> SEQUENCE: 1

Thr Ala Val Ser Pro Thr Thr Leu Arg
1               5

<210> SEQ ID NO 2
<211> LENGTH: 9
<212> TYPE: PRT
<213> ORGANISM: Unknown
<220> FEATURE:
<223> OTHER INFORMATION: Chemically Synthesized

<400> SEQUENCE: 2

Thr Ser Phe Asn Met Asp Thr Leu Ala
1               5

<210> SEQ ID NO 3
<211> LENGTH: 9
<212> TYPE: PRT
<213> ORGANISM: Unknown
<220> FEATURE:
<223> OTHER INFORMATION: Chemically Synthesized

<400> SEQUENCE: 3

Thr Ser Phe Ser Pro Thr Thr Leu Arg
1               5

<210> SEQ ID NO 4
<211> LENGTH: 9
<212> TYPE: PRT
<213> ORGANISM: Unknown
<220> FEATURE:
<223> OTHER INFORMATION: Chemically Synthesized

<400> SEQUENCE: 4

Thr Ser Phe Asn Pro Thr Thr Leu Arg
1               5

<210> SEQ ID NO 5
<211> LENGTH: 9
<212> TYPE: PRT
<213> ORGANISM: Unknown
<220> FEATURE:
<223> OTHER INFORMATION: Chemically Synthesized

<400> SEQUENCE: 5

Thr Ser Phe Asn Met Thr Thr Leu Arg
1               5

<210> SEQ ID NO 6
<211> LENGTH: 9
<212> TYPE: PRT
<213> ORGANISM: Unknown
<220> FEATURE:
<223> OTHER INFORMATION: Chemically Synthesized

<400> SEQUENCE: 6

Thr Ser Phe Asn Met Asp Thr Leu Arg
1               5

```
<210> SEQ ID NO 7
<211> LENGTH: 9
<212> TYPE: PRT
<213> ORGANISM: Unknown
<220> FEATURE:
<223> OTHER INFORMATION: Chemically Synthesized

<400> SEQUENCE: 7

Thr Ser Phe Asn Met Asp Thr Leu Ala
1               5

<210> SEQ ID NO 8
<211> LENGTH: 45
<212> TYPE: DNA
<213> ORGANISM: Unknown
<220> FEATURE:
<223> OTHER INFORMATION: Chemically Synthesized

<400> SEQUENCE: 8
gggtgttata gagtgcacgt catttagccc gacaactctg agaac           45

<210> SEQ ID NO 9
<211> LENGTH: 45
<212> TYPE: DNA
<213> ORGANISM: Unknown
<220> FEATURE:
<223> OTHER INFORMATION: Chemically Synthesized

<400> SEQUENCE: 9
gggtgttata gagtgcacgt catttaatcc gacaactctg agaac           45

<210> SEQ ID NO 10
<211> LENGTH: 45
<212> TYPE: DNA
<213> ORGANISM: Unknown
<220> FEATURE:
<223> OTHER INFORMATION: Chemically Synthesized

<400> SEQUENCE: 10
gggtgttata gagtgcacgt catttaatat gacaactctg agaac           45

<210> SEQ ID NO 11
<211> LENGTH: 45
<212> TYPE: DNA
<213> ORGANISM: Unknown
<220> FEATURE:
<223> OTHER INFORMATION: Chemically Synthesized

<400> SEQUENCE: 11
gagtgcacgt catttaatat ggacactctg agaacagaag tggta           45

<210> SEQ ID NO 12
<211> LENGTH: 45
<212> TYPE: DNA
<213> ORGANISM: Unknown
<220> FEATURE:
<223> OTHER INFORMATION: Chemically Synthesized

<400> SEQUENCE: 12
tcatttaata tggacactct ggcaacagaa gtggtaaaga ccttc           45
```

VIRULENCE DETERMINANT WITHIN THE E2 STRUCTURAL GLYCOPROTEIN OF CLASSICAL SWINE FEVER VIRUS

BACKGROUND OF THE INVENTION

1. Field of the Invention

This invention relates to the isolation and characterization of novel Classical Swine Fever Virus (CSFV) virulence determinants within the E2 structural glycoprotein and utilization of these novel virulence determinants to design live attenuated CSF vaccines.

2. Description of the Relevant Art

Classical swine fever (CSF) is a highly contagious disease of swine that can be either acute or chronic in nature (van Oirschot, J. T. 1986. In: *Diseases of Swine*, 6th edition, Leman et al., eds., Iowa State University Press, Ames, Iowa, page 289). The etiological agent, CSF virus (CSFV), is a small, enveloped virus with a positive, single-stranded RNA genome and, along with bovine viral diarrhea virus (BVDV) and border disease virus (BDV), is classified as a member of the genus Pestivirus within the family Flaviridae (Hulst et al. 2001. *J. Virol.* 75: 9585-9595). The 12.5 kb CSFV genome contains a single open reading frame which encodes a 4000 amino acid polyprotein and ultimately yields 11 to 12 final cleavage products (NH2-Npro-C-Erns-E1-E2-p7-NS2-NS3-NS4A-NS4B-NS5A-NS5B-COOH) through co- and post-translational processing of the polyprotein by cellular and viral proteases (Rice, C. M. 1996. In: *Fundamental Virology*, 3rd edition, Fields and Howley, eds., Lippincott Raven, Philadelphia, pp. 931-959).

Virulence and host range phenotypes vary among CSFV isolates and between pestiviruses. Infection with highly virulent CSFV strains leads to death in infected animals, whereas isolates of moderate to low virulence induce a prolonged chronic disease (van Oirschot, supra). In addition, BVDV and BDV, while etiologic agents of diseases in bovine and ovine species, respectively, can also infect swine without inducing clinical disease (van Oirschot, supra). Despite availability of genomic sequences from CSFV of differing virulence phenotypes, BVDV, and BDV, the genetic basis of CSFV virulence in the natural host remains poorly understood (van Oirschot, supra). The use of reverse genetics has enabled the identification of viral determinants of virulence facilitating development of candidate live attenuated CSF vaccines (Mayer et al. 2004. *Vaccine* 22: 317-328; Meyers et al. 1999. *J. Virol.* 73: 10224-10235; Moorman et al. 1996. *J. Virol.* 70: 763-770; Moser et al. 2001. *Virus Genes* 23: 63-68; Risatti et al. 2005a. *J. Virol.* 79: 3787-3796; Risatti et al. 2005b. *Virology* 343: 116-117; Ruggli et al. 1996. *J. Virol.* 70: 3478-3487; Tratschin et al. 1998. *J. Virol.* 72: 7681-7684; van Gennip et al. 2000. *Vaccine* 19: 447-459).

The capsid protein, and glycoproteins Erns, E1, and E2 are the structural components of the CSFV virion with E1 and E2 anchored to the envelope by their carboxyl termini and Erns loosely associated with the viral envelope (Thiel et al. 1991. *J. Virol.* 65: 4705-4712; Weiland et al. 1990. *J. Virol.* 64: 3563-3569; Weiland et al. 1999. *J. Gen. Virol.* 80: 1157-1165). All three glycoproteins have been associated with CSFV virulence (Meyers, supra; Risatti et al. 2005 a, b, supra).

E2 glycoprotein is considered essential for CSFV replication, as virus mutants containing partial or complete deletions of the E2 gene have proven non-viable (van Gennip et al. 2002. *Vaccine* 20: 1544-1556). E2 has been implicated, along with Erns (Mayer et al., supra) and E1 (Wang et al. 2004. *Virology* 330: 332-341), in viral adsorption to host cells; indeed, chimeric pestiviruses exhibit infectivity and cell tropism phenotypes consistent with those of the E2 gene donor (van Gennip et al. 2000, 2002, supra). E2 is the most immunogenic of the CSFV glycoproteins (Konig et al. 1995. *J. Virol.* 69: 6479-6486; Weiland et al. 1990, supra), inducing neutralizing antibodies and protection against lethal challenge. CSFV E2 also contains, between residues 829 and 837, an epitope recognized by monoclonal antibody (mAb) WH303 (Lin et al. 2000. *J. Virol.* 74:11619-11625), a reagent which fails to react with BVDV or BDV E2 and is routinely used for CSF diagnostics.

Here we report the effects of mutations within the WH303 epitope of CSFV E2, mutations which change the amino acid sequence of the virulent Brescia CSFV progressively toward the homologous amino acid sequence of BVDV strain NADL, demonstrating an additive effect for viral virulence in swine and complete attenuation after six amino acid changes. Such attenuate viruses permit the rational design of live attenuated CSF vaccines. Animals infected with virus mutants were protected when challenged with virulent Brescia virus at 3 and 21 days post vaccination. Modification at this site within the WH303 epitope allows development of a diagnostic test to differentiate vaccinated from infected animals.

SUMMARY OF THE INVENTION

We have identified a novel CSFV virulence determinant within the E2 glycoprotein.

In accordance with this discovery, it is an object of the invention to provide a recombinant classical swine fever virus (CSFV) comprising DNA encoding a modified CSFV E2 glycoprotein.

It is also an object of the invention to provide a recombinant classical swine fever virus comprising DNA encoding CSFV E2 glycoprotein which has been modified by progressively mutating a portion of the E2 gene of the highly pathogenic strain Brescia, resulting in the mutated E2 virus more closely resembling the WH303 epitope sequence of the homologous E2 gene from BVDV, a modification resulting in attenuation of CSFV.

An added object of the invention is to provide immunogenic compositions comprising a viable recombinant classical swine fever virus comprising a modified CSFV E2 glycoprotein.

An additional object of the invention is to provide a rationally designed live attenuated CSFV vaccine which lessens severity of CSF.

Another object of the invention is to provide a rationally designed live attenuated CSFV vaccine effective to protect an animal from clinical CSF disease when challenged with virulent Brescia CSFV.

A further object of the invention is to provide a marker vaccine which allows a serological distinction between vaccinated animals and animals infected with CSFV.

A still further object of the invention is to provide a method for protecting an animal against CSF by administering an effective amount of rationally designed live attenuated CSFV vaccine.

Other objects and advantages of this invention will become readily apparent from the ensuing description.

BRIEF DESCRIPTION OF THE DRAWINGS

FIGS. 2A and 2B compare characteristics of T1v-T5v mutants and BICv.

DETAILED DESCRIPTION OF THE INVENTION

The development of disease control strategies in the event of a CSFV outbreak requires rapid onset of protection, which becomes a more important parameter of vaccine performance than, for example, duration of protection. The development of such vaccines would imply the production of rationally designed live attenuated vaccine CSFV strains.

The genetic basis and the molecular mechanisms underlying Pestivirus virulence are still unclear. In the case of CSFV, different reports have described associations between viral proteins or specific genomic region with virulence. Single or double codon mutations abrogating RNase activity of CSFV strain Alfort Erns glycoprotein, attenuated the virus in pigs (Meyers et al., supra). Similar results were also observed by mutating the RNase domain of BVDV Erns glycoprotein (Meyer et al. 2002. *J. Virol.* 76: 8494-8503). More recently, it has been shown that deleting Npro from CSFV virulent strains Alfort/187 and Eystrup resulted in attenuated viruses in swine (Mayer et al., supra). An amino acid substitution in CSFV E2 glycoprotein associated with three amino acid substitutions in Erns resulted in reduced virulence in pigs (van Gennip et al. 2004. *J. Virol.* 78: 8812-8823). Additionally, an in frame insertion of 19 amino acids into E1 gene of CSFV strain Brescia led to attenuation in vivo (Risatti et al. 2005b, supra). CSFV E2 has also been implicated in virulence. The replacement of the E2 gene in CSFV strain Brescia with the E2 gene from vaccine strain CS resulted in a chimeric virus that has a significant in vivo attenuation (Risatti et al. 2005a, supra). None of the 22 amino acids substitutions in CS vaccine virus E2 protein, compared to the sequence of Brescia E2 protein, affect mAb WH 303 epitope. All three viruses, Brescia, CS and the chimera, react strongly with mAb 303 suggesting the existence, of another genetic determinant associated with CSFV attenuation.

Here, we show that mutations introduced into mAb WH 303 epitope in E2 glycoprotein of highly pathogenic CSFV strain Brescia resulted in attenuation of the virus. Progressive changes were introduced CSFV Brescia WH 303 epitope (TAVSPTTLR; SEQ ID NO:1) to resemble residues found at the same position (TSFNMDTLA; SEQ ID NO:2) in BVDV strain NADL E2 glycoprotein. Interestingly, TSFNMDTLR (T4v) or TSFNMDTLA (T5v) lack reactivity to mAb WH 303, show small plaque morphology, and are significantly attenuated in vivo. Unlike the acute fatal disease induced by BICv, T4v and T5v infection was sub-clinical, characterized by decreased viral replication in target organs and reduced virus shedding.

The relevance of WH 303 as a major immunodominant epitope have been recently observed during characterization of neutralizing monoclonal antibodies to CSFV E2 and Erns using phage-displayed random peptide library (Zhang et al. 2006. *Archives of Virology* 151 (1): 37-54). Those monoclonal antibodies were found to bind a common motif SPTxL that also map to WH 303 epitope (SPTTL). Furthermore, multi peptide-vaccines, containing the WH 303 epitope, consisting of six overlapping peptides ranging between 20 to 25 amino acids length induced immunity against CSFV (Dong et al. 2005. *Vaccine* 23:3630-3633).

Attenuation of T5v in pigs conceivably could involve some aspect of virus attachment and/or efficient entry into critical target cells in vivo. Erns, E1 and E2 are structural glycoproteins in the CSFV virion envelope (Thiel et al., supra). Anchored to the envelope, E2 appears as both homo and heterodimers linked by disulfide bridges (Thiel et al., supra, Weiland et al. 1990, 1999, supra) and, along with Erns (Hulst et al. 1997. *J. Gen. Virol.* 78: 2779-2787) and E1 (Wang et al., supra) have been shown to be important for virus reception. Engineered Pestiviruses containing chimeric E2 proteins have altered host range. A chimeric BVDV harboring the complete E2 gene from Border Disease Virus (BDV), a sheep Pestivirus, lost its ability to form plaques in bovine kidney cells (MDBK) but retained its ability to form plaques in sheep cells (Lian et al. 2003. *J. Gen. Viol.* 84: 1269-1274). However, MDBK cells were still permissive to the chimera although the difference in viral progeny yield, 24 hours after infection, was 100 fold less than wild type BVDV. Likewise, partial replacement of the amino terminus of CSFV C strain E2 with the homologous sequence from BVDV resulted in 10 fold decrease of virus progeny yield in swine kidney cells (SK6). SK6 cells were similarly permissive for the chimera and BVDV E2 donor; however, the chimera did not gain BVDV ability to infect fetal bovine epithelial cells (van Gennip et al. 2000, supra). Similarly, T4v and T5v presented a 10 fold viral progeny yield reduction in SK6 cells in comparison with BICv, T1v, T2v and T3v (FIG. 2A), and lack the ability to replicate efficiently in bovine kidney cells (MDBK) (data not shown).

Figure 2A:
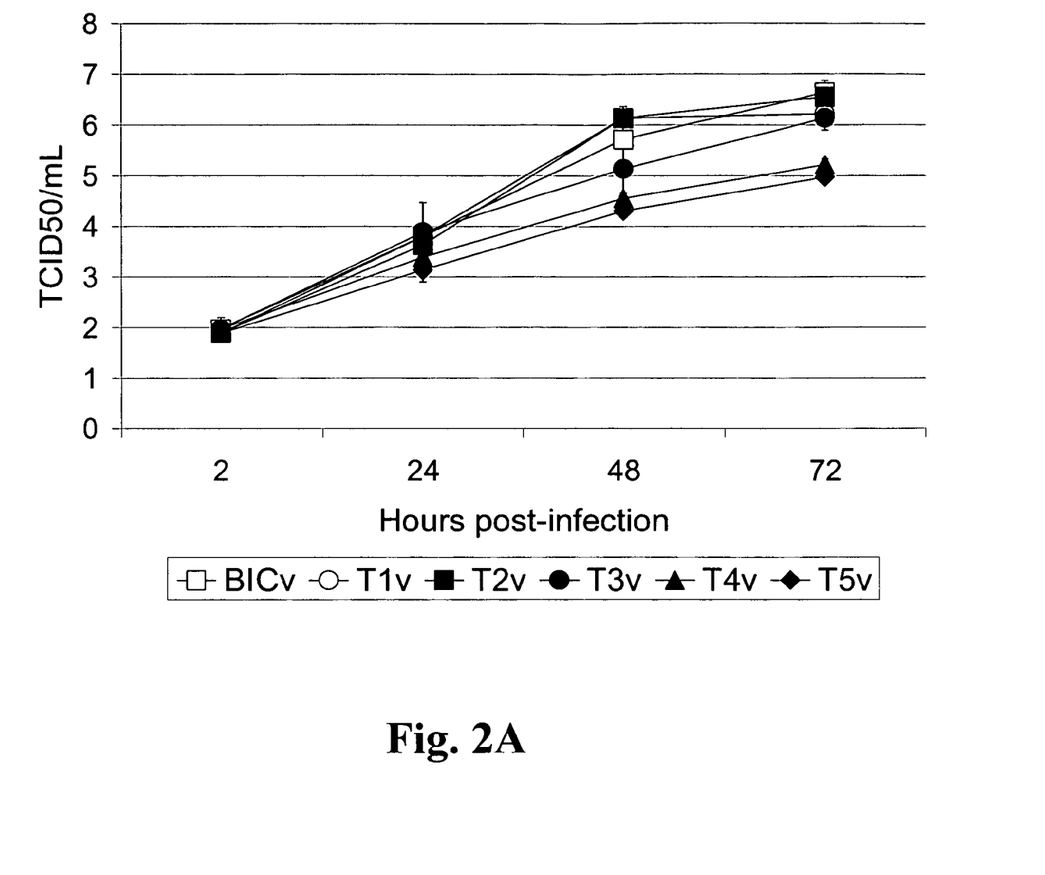
FIG. 2A shows in vitro growth characteristics of T1v-T5v mutants and BICv. SK6 monolayers were infected (MOI=0.01) with T1v, T2v, T3v, T4v, T5v or BICv and virus yield titrated at times post infection. Data represent means and standard deviations from two independent experiments.
Figure 2B:
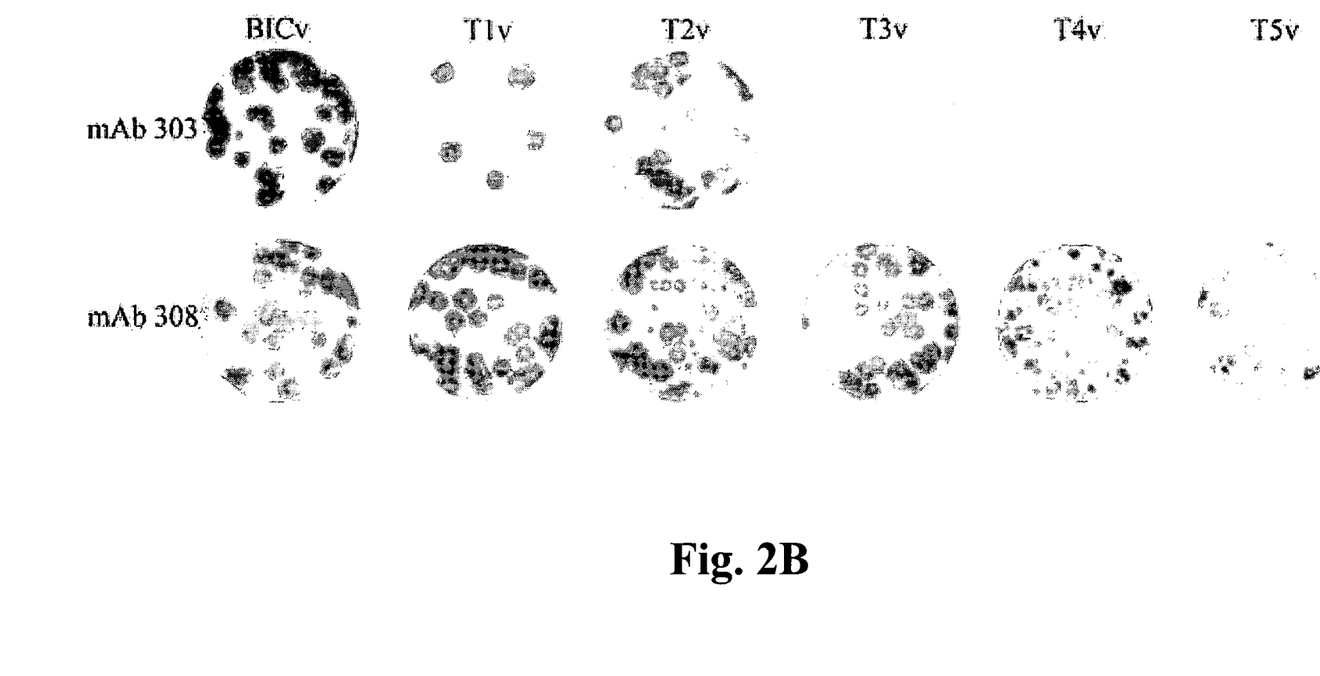
FIG. 2B shows plaque formation and mAb reactivity of mutants T1v-T5v and BICV. SK6 monolayers were infected with 50 to 100 TCID$_{50}$, overlaid with 0.5% agarose and incubated at 37° C. for 3 days. Plates were fixed with 50% (vol/vol) ethanol-acetone and differentially stained by immunohistochemistry with mAb WH303 and mAb WH308.

T4v and T5v exhibited an approximately 70% plaque size reduction compared with parental BICv in SK6 cells (FIG. 2B). A similar small plaque phenotype was observed with BVDV strain NADL on SK6 cells (data not shown), suggesting that these viruses have an in vitro altered capability of attachment and/or spreading. Although, an association between in vitro plaque size reduction and in vivo attenuation of CSFV is yet to be established, there are some observations that suggest a relationship. Hulst et al. (J. Virol 74:9553-9561; Hulst et al. 2001, supra) have observed that CSFV Brescia heparin sulfate binding dependent variants obtained after serial passages in cultured swine kidney cells have a reduced plaque size. These variants, containing a single amino acid mutation in the Erns protein, were virulent in pigs (Hulst et al. 2000, 2001, supra). However, two different CSFV strain Brescia derived recombinant viruses containing mutations in E1 (Risatti et al. 2005b, supra) and E2 (Risatti et al. 2005a, supra) showed reduced plaque size phenotype in cultured swine kidney cells and were attenuated in swine.

In summary, a novel CSFV genetic virulence determinant associated with E2 glycoprotein has been identified. Although the mechanism underlying the attenuation remains unknown, interestingly, the gradual loss of reactivity with the mAb WH 303 correlated with a loss of virulence in vivo, leading to the final attenuation of CSFV, suggesting a link between the lack of the epitope sequence and the inability to induce disease by other pestiviruses (BVDV and BDV) in swine. Improving the understanding of the genetic basis of CSFV virulence will permit rational design of live attenuated CSF vaccines of enhanced safety, efficacy and utility. Additionally, in the particular case of viruses T4v and T5v the lack of reactivity with mAb WH303, which recognize a highly specific and conserved CSFV epitope, opens the potential use of those viral mutants as attenuated marker vaccine.

EXAMPLES

Having now generally described this invention, the same will be better understood by reference to certain specific examples, which are included herein only to further illustrate the invention and are not intended to limit the scope of the invention as defined by the claims.

Example 1

Viruses and Cell Cultures

Swine kidney cells (SK6) (29), free of BVDV, were cultured in Dulbecco' minimal essential medium (DMEM) (Gibco, Grand Island, N.Y.) with 10% fetal calf serum (FCS) (Atlas Biologicals, Fort Collins, Colo.). CSFV Brescia strain was propagated in SK6 cells and used for the construction of an infectious cDNA clone (17). Titration of CSFV from clinical samples was performed using SK6 cells in 96 well plates (Costar, Cambridge, Mass.). Viral infectivity was detected, after 4 days in culture, by immunoperoxidase assay using the CSFV monoclonal antibodies WH303 or WH308 (1) and the Vectastain ABC kit (Vector Laboratories, Buringames, Calif.) (25). Titers were calculated using the method of Reed and Muench (14) and expressed as TCID50/ml. As performed, test sensitivity was >1.8 TCID50/ml.

Example 2

Construction of CSFV Infectious Clones T1-T5

Figure 1:
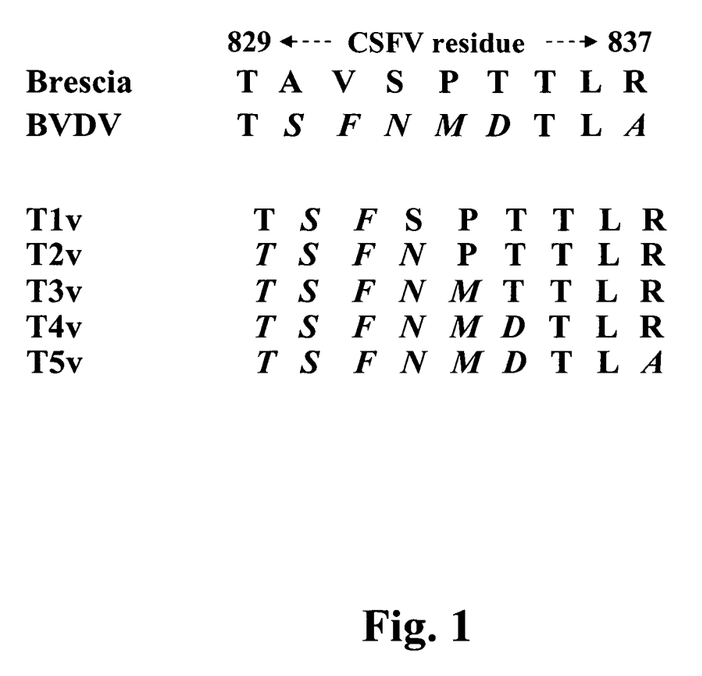
FIG. 1 depicts a comparison of CSFV Brescia, BVDV strain NADL and CSFV T1-5 mutant viruses in the mAb WH303 epitope area of E2 glycoprotein. Amino acid residue positions in the CSFV polyprotein are indicated. Italics indicate residues different from those in Brescia E2, both in BVDV strain NADL and CSFV T1v to T5v.

A full-length infectious clone (IC) of the virulent Brescia isolate (pBIC) (17) was used as a template in which six residues of the WH303 epitope (TAVSPTTLR; SEQ ID NO:1) between residues 829 to 837 of E2 were mutated to reflect those of homologous residues present in the BVDV isolate NADL (TSFNMDTLA; SEQ ID NO:2) (Lin et al., supra). Mutations were added progressively, yielding five IC for rescue of the following viral mutants: T1v (TSFSPTTLR; SEQ ID NO:3), T2v (TSFNPTTLR; SEQ ID NO:4), T3v (TSFNMTTLR; SEQ ID NO:5), T4v (TSFNMDTLR; SEQ ID NO:6) and T5v (TSFNMDTLA; SEQ ID NO:7) (FIG. 1). Mutations were introduced by site directed mutagenesis using the QuickChange XL Site-Directed Mutagenesis kit (Stratagene, Cedar Creek, Tex.) performed per manufacturers instructions and using primers and target plasmids described in Table 1.

TABLE 1

Primers used to construct T1-T5 viruses.

| Primers* | Sequence | SEQ ID NO: |
|---|---|---|
| T1F | 5'-GGGTGTTATAGAGTGCACGTCATTTAGCCCGACAAC TCTGAGAAC-3' | 8 |
| T2F | 5'-GGGTGTTATAGAGTGCACGTCATTTAATCCGACAAC TCTGAGAAC-3' | 9 |
| T3F | 5'-GGGTGTTATAGAGTGCACGTCATTTAATATGACAAC TCTGAGAAC-3' | 10 |
| T4F | 5'-GAGTGCACGTCATTTAATATGGACACTCTGAGAACA GAAGTGGTA-3' | 11 |
| T5F | 5'-TCATTTAATATGGACACTCTGGCAACAGAAGTGGTA AAGACCTTC-3' | 12 |

*Only forward primer sequences are provided. Reverse primers correspond to the complementary sequence.

Infectious RNA was in vitro transcribed from a full-length ICs of CSFV strain Brescia or mutants T1 to T5 and used to transfect SK6 cells (FIG. 1A). Virus was rescued from transfected cells by day 4 post-transfection. Nucleotide sequences of the rescued virus genomes were identical to parental DNA plasmids, confirming that only mutations at the locus encoding the WH303 epitope were reflected in T1v-T5v.

Example 3

In Vitro Rescue of CSFV Brescia and T1-T5v Mutant Viruses

Full-length genomic infectious clones were linearized with SrfI and in vitro transcribed using the T7 Megascript system (Ambion, Austin, Tex.). RNA products were precipitated with LiCl and transfected into SK6 cells by electroporation at 500 volts, 720 ohms, 100 watts with a BTX 630 electroporator (BTX, San Diego, Calif.). Cells were plated in 12 well plates and 25 cm² flasks, and incubated for 4 days at 37° C. and 5% $CO_2$ atmosphere. Virus was detected by immunoperoxidase staining using a CSFV E2 specific monoclonal antibody (WH308). Stocks of rescued viruses were stored at −70 C. Accuracy of the introduced mutations was verified by sequencing the E2 gene of the mutated viruses.

Example 4

In Vitro and In Vivo Analysis of T1v-T5v

In vitro growth characteristics of T1v-T5v relative to parental pBICv were evaluated in a multistep growth curve (FIG. 2A). SK6 cell cultures were infected at a multiplicity of infection (MOI) of 0.01 $TCID_{50}$ per cell. Virus was adsorbed for 1 h (time zero), and samples were collected at times post infection through 72 h. While mutants T1v, T2v, and T3 exhibited growth characteristics practically indistinguishable from pBICv, T4 and T5v exhibited a 10-fold decrease in the final virus yield. T4v and T5v also exhibited an 80-90% reduction in plaque size relative to BICv, T1v, T2v, and T3v (FIG. 2B). Finally, while immunocytochemical reactivity with the MAb WH303 was equivalent for T1v, T2v, and pBICv, reactivity was partially lost in T3v and completely abolished in T4v and T5v infected cells (FIG. 2B). These results indicate that mutations of the WH303 epitope affecting the ability of CSFV to replicate in vitro have a similar affect on WH303 reactivity.

To examine the effect progressive WH303 epitope mutation on CSFV virulence in swine, virulence phenotypes of T1v-T5v mutant and BICv wild type viruses were compared in 6 groups of Yorkshire pigs intranasally inoculated with 105 TCID50 of virus and monitored for clinical disease. Results from this experiment are shown in Table 2 and FIGS. 3-5. Identity and stability of WH303 epitope mutations were confirmed by nucleotide sequence analysis of virus recovered from tonsils of T1v-T5v-infected animals at 6 DPI (data not shown).

(Table 3). T3v induced lethal disease but with delayed kinetics relative to BICv, as death occurred 4-8 days later (Table 2). Remarkably, T4v and T5v failed to induce lethal disease, with T4v inducing only a mild and transient fever and T5v inducing almost no clinical disease (Table 2, FIG. 3). Similarly, BICv, T1v, T2v and T3v infection resulted by 6 DPI in a drastic reduction in white blood cell (WBC) and platelet counts which remained low until death, while T4v and T5v-infected induced a transient and much less dramatic effect (FIG. 4).

TABLE 3

Virus titers[1] in clinical samples and tissues following infection with T5v or BICv.

| | Virus | | | | | | | | | |
|---|---|---|---|---|---|---|---|---|---|---|
| | T5v | | | | | BICv | | | | |
| | DPI[2] | | | | | | | | | |
| | 2 | 4 | 6 | 8 | 14 | 2 | 4 | 6 | 8 | 14 |
| Nasal Swab | Neg[3] | 1.97 | Neg | Neg | Neg | Neg | Neg | 1.97 | 4.63 | 3.97 |
| Tonsil Scrapings | Neg | Neg | 2.63 | Neg | Neg | Neg | Neg | 1.97 | 4.97 | 2.97 |
| Blood | Neg | ND[4] | 2.97 | 3.97 | Neg | Neg | 3.13 | 6.47 | 6.30 | 6.80 |
| Tonsil | 2.13 | 2.97 | 3.30 | 1.97 | 2.80 | 1.97 | 4.63 | 5.13 | 5.47 | 6.13 |
| Mandibular LymphNode | 2.80 | 3.30 | 3.63 | 2.47 | 3.30 | 1.80 | 2.80 | 4.80 | 5.80 | 5.97 |
| Spleen | Neg | 2.97 | 2.63 | 3.47 | 2.80 | Neg | 2.13 | 2.80 | 5.63 | 6.30 |
| Kidney | Neg | 2.47 | 2.97 | 3.13 | 2.13 | Neg | Neg | 2.80 | 4.80 | 5.97 |

[1]Titers expressed as $TCID_{50}$/ml
[2]DPI, days post-infection
[3]Neg: ≤1.80 $TCID_{50}$/ml
[4]ND: Not Determined

TABLE 2

Swine survival and fever response following infection with T1-T5v or BIC$_v$.

| Virus | Survivors/ Total | Mean time To Death Days (SD) | Mean time Fever Onset Days (SD) | Mean time Duration Fever Days (SD) | Avg. Max Daily Temp. (SD) |
|---|---|---|---|---|---|
| T1v | 0/2 | 8.5 (2.1) | 3.0 (1.4) | 4.5 (2.1) | 107.2 (0.0) |
| T2v | 0/2 | 14.5 (2.1) | 4.5 (0.7) | 9.5 (0.7) | 106.6 (1.7) |
| T3v | 0/2 | 19.0 (0.0) | 5.0 (0.0) | 6.0 (1.4) | 105.7 (1.6) |
| T4v | 4/4 | — | 5.0 (0.0) | 2.5 (2.1)* | 106.2 (0.6) |
| T5v | 6/6[#] | — | — | — | 104.8 (0.6) |
| BIC$_v$ | 0/2[#] | 12.5 (2.1) | 4.5 (0.7) | 4.5 (0.7) | 105.8 (0.3) |

*Two out of 4 animals presented fever.
[#]Includes animals used in protection studies.

Figure 3:
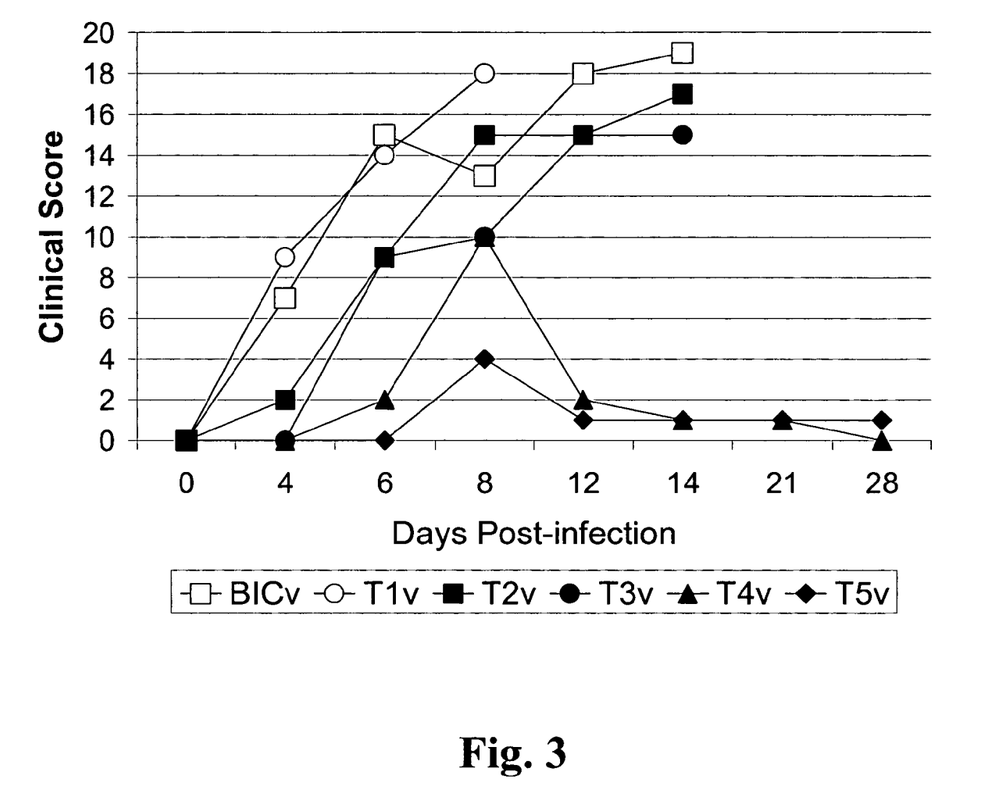
FIG. 3 shows clinical scores recorded from pigs infected with recombinant viruses T1v-T5v and BICv. Clinical Scores were calculated as previously described with modifications and were based on observations of two (T1v, T2v, T3v and T4v) or six (T5v and BICv) animals.
Figure 4:
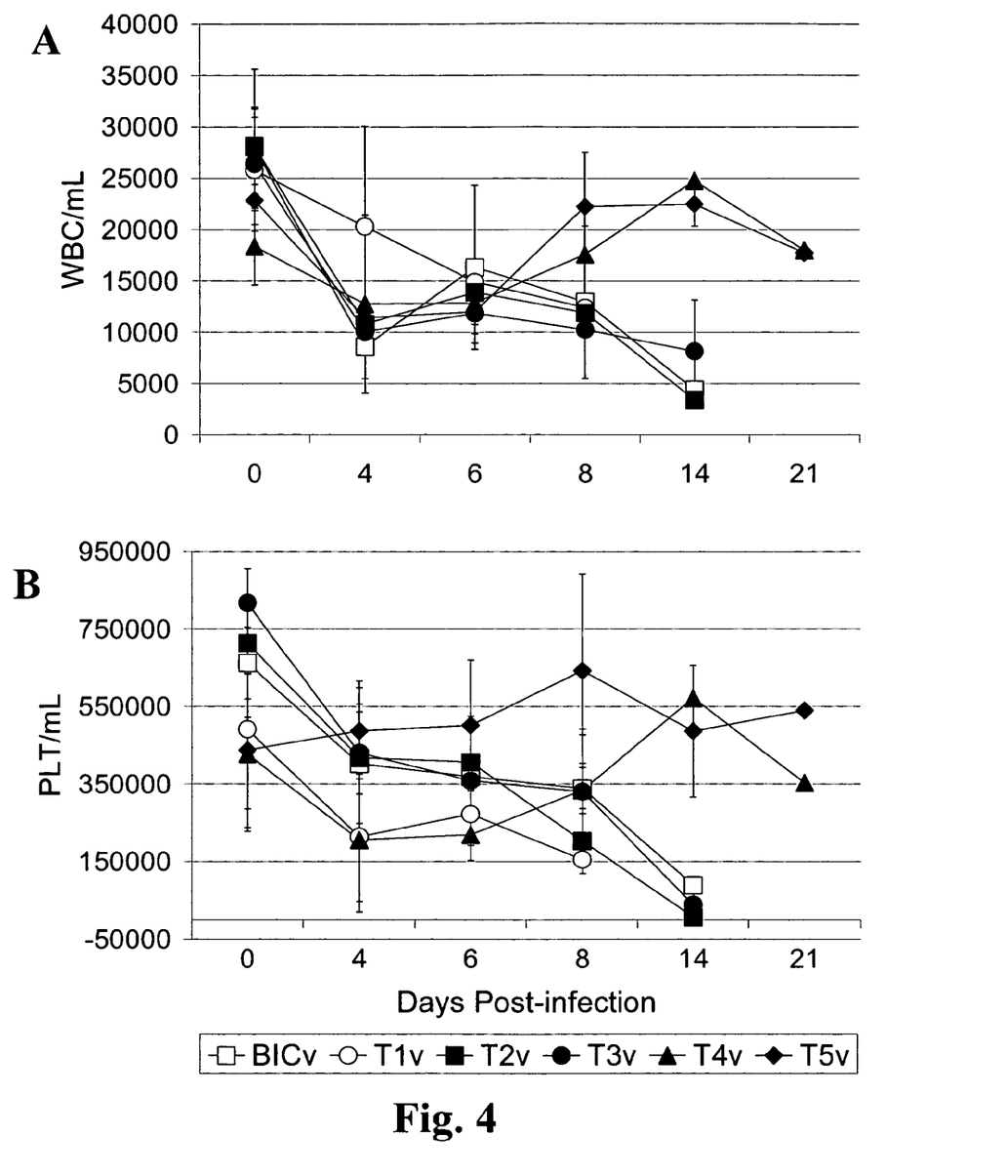
FIGS. 4A-B show peripheral white blood cell (FIG. 4A) and platelet counts (FIG. 4B) in pigs infected with recombinant viruses T1v-T5v and BICv. Counts are expressed as numbers/ml and each point represents the mean and standard errors for two (T1v, T2v, T3v and T4v) or six (T5v and BICv) animals.
Figure 5:
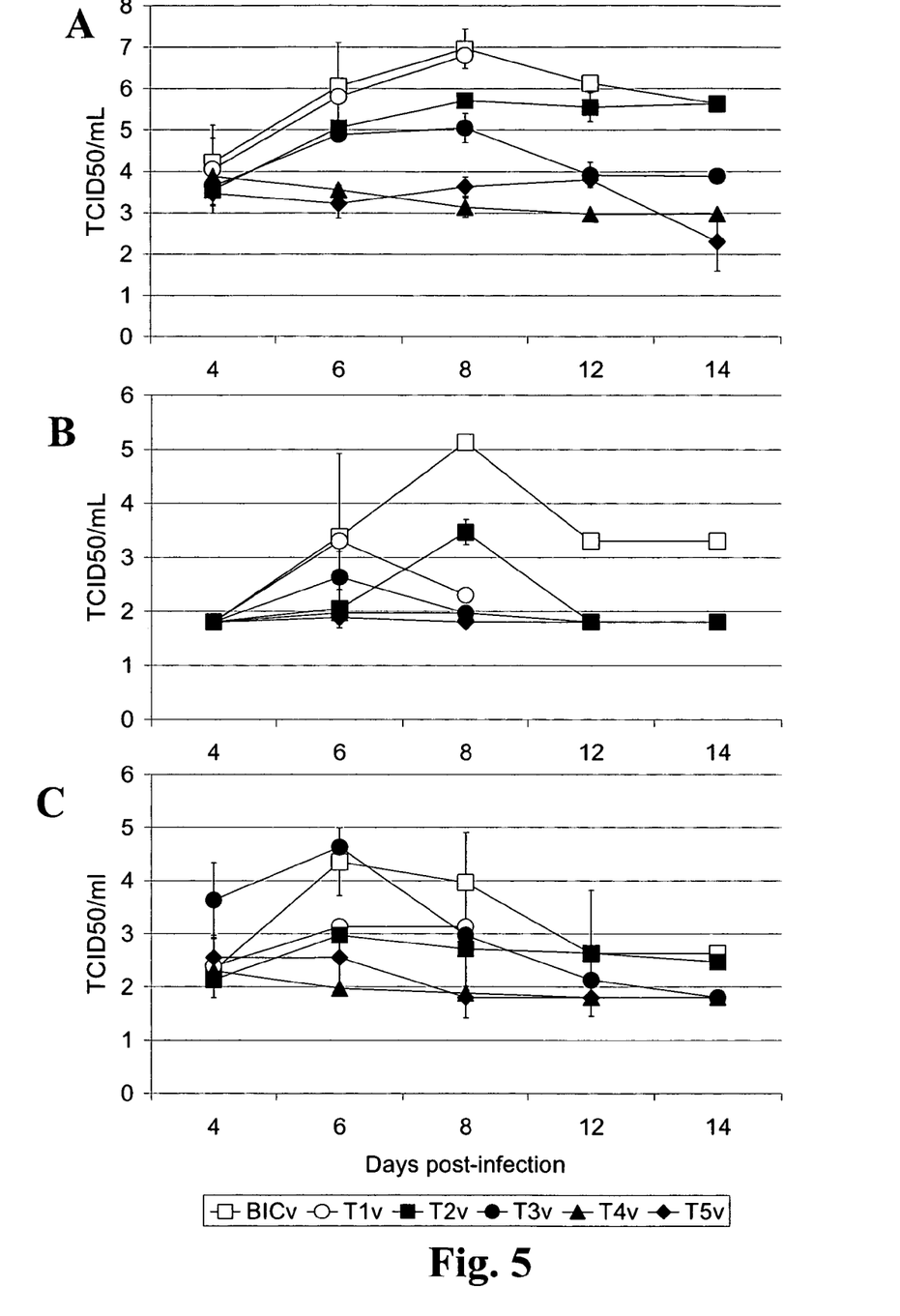
FIGS. 5A-C depict virus titers in blood (FIG. 5A), nasal swabs (FIG. 5B), and tonsil scrapings (FIG. 5C) from pigs infected with T1v-T5v mutants or BICv. Each point represents the mean TCID$_{50}$/mL and standard deviation for two (T1v, T2v, T3v and T4v) or six (T5v and BICv) animals.

While BICv, as expected, was highly pathogenic, effectively inducing fever, clinical signs, and death in swine, T1v-T5v mutants appeared to have virulence phenotypes that were increasingly attenuated (Table 2, FIG. 3). T1v and T2v were also highly pathogenic, inducing fever and death in swine in a manner similar to that of BICv (Table 2); however, T2v demonstrated a slight delay in clinical scores relative to BICv Attenuation of T1v-T5v was also reflected in viremia and virus shedding. While T1v and T2v induced viremic titers comparable to those induced by BICv, T3v titers were reduced by $10^1$ to $10^2$ $\log_{10}$, and T4v and T5v induced titers $10^3$ to $10^5$ $\log_{10}$ lower than BICv titers at similar times post-infection (FIG. 5A). A similar pattern was observed for virus titers from nasal swabs and tonsil-scrapings (FIGS. 5B and C, respectively), with T3v, T4v and T5v titers falling below detectible levels at later DPI.

For a more detailed study of T5v pathogenesis, T5v and BICv-infected animals were euthanized at 2, 4, 6, 8, and 14 DPI (one animal/time point/group) and virus titers determined for tissue samples of tonsils, submandibular lymph node, spleen, blood and kidney tissue samples and for nasal swab and tonsil scraping samples (Table 3). T5v exhibited significantly lower levels of virus replication in tonsils (approximately $10^2$ to $10^4$ $\log_{10}$) relative to BICv. Similar differences between T5v and BICv were observed in virus titers from the regional draining mandibular lymph node, spleen and kidney between (Table 3).

These results indicate that an increased number of mutations within the WH303 epitope of CSFV E2 had an additive effect in attenuating the virus for swine, with mutations present in T4v and T5v resulting in significant decrease in viral virulence. Furthermore, T5v infection is characterized by a very mild and transient clinical disease, decreased viral replication in tonsils and target tissues, and dramatically reduced virus shedding.

Example 5

DNA Sequencing and Analysis

Full-length infectious clones, in vitro rescued viruses, and viruses recovered from infected animals were completely sequenced with CSFV specific primers by the dideoxynucleotide chain-termination method (Sanger et al. 1977. *Proc. Natl. Acad. Sci. USA* 74: 5463-5467). Sequencing reactions were prepared with the Dye Terminator Cycle Sequencing Kit (Perkin-Elmer, Boston, Mass.). Reaction products were sequenced on a PRISM 3730xl automated DNA Sequencer (PE Biosystems, Foster City, Calif.). Sequence data were assembled with the Phrap software program (www-.phrap.org), with confirmatory assemblies performed using CAP3. The final DNA consensus sequence represented, on average, five-fold redundancy at each base position. Sequence comparisons were conducted using BioEdit.

Example 6

Animal Infections

Each of the T1v-T5v mutants was initially screened for its virulence phenotype in swine relative to virulent Brescia virus. Swine used in all animal studies here were 10 to 12 week old, forty-pound pigs inoculated intranasally with $10^5$ TCID$_{50}$ of either mutant or wild-type virus. For screening, 12 pigs were randomly allocated into 6 groups of 2 animals each, and pigs in each group were inoculated with one of the T1v-T5v mutants or pBICv. Clinical signs (anorexia, depression, fever, purple skin discoloration, staggering gait, diarrhea and cough) were observed daily throughout the experiment and scored as previously described with modifications.

To assess the effect of T5v mutations on virus shedding and distribution in different organs during infection, 10 pigs were randomly allocated into 2 groups of 5 animals each and inoculated with T5v or pBICv. One pig per group was sacrificed at 2, 4, 6, 8 and 14 DPI. Blood, nasal swabs and tonsil scraping samples were obtained from pigs at necropsy. Tissue samples (tonsil, mandibular lymph node, spleen and kidney) were snap-frozen in liquid nitrogen for virus titration.

For protection studies, 12 pigs were randomly allocated into 3 groups of 4 animals each. Pigs in groups 1 and 2 were inoculated with T5v, animals in group 3 were mock infected. At 3 DPI (group 1) or 21 DPI (group 2), animals were challenged with BICv along with animals in group 3. Clinical signs and body temperature were recorded daily throughout the experiment as described above. Blood, serum, nasal swabs and tonsil scrapings were collected at times after challenge, with blood obtained from the anterior vena cáva in EDTA containing tubes (Vacutainer) for total and differential white blood cell counts. Total and differential white blood cell and platelet counts were obtained using a Beckman Coulter ACT (Beckman, Coulter, Calif.).

Example 7

T5v Infection Protects Swine Against Challenge with Pathogenic BICv

Figure 6:
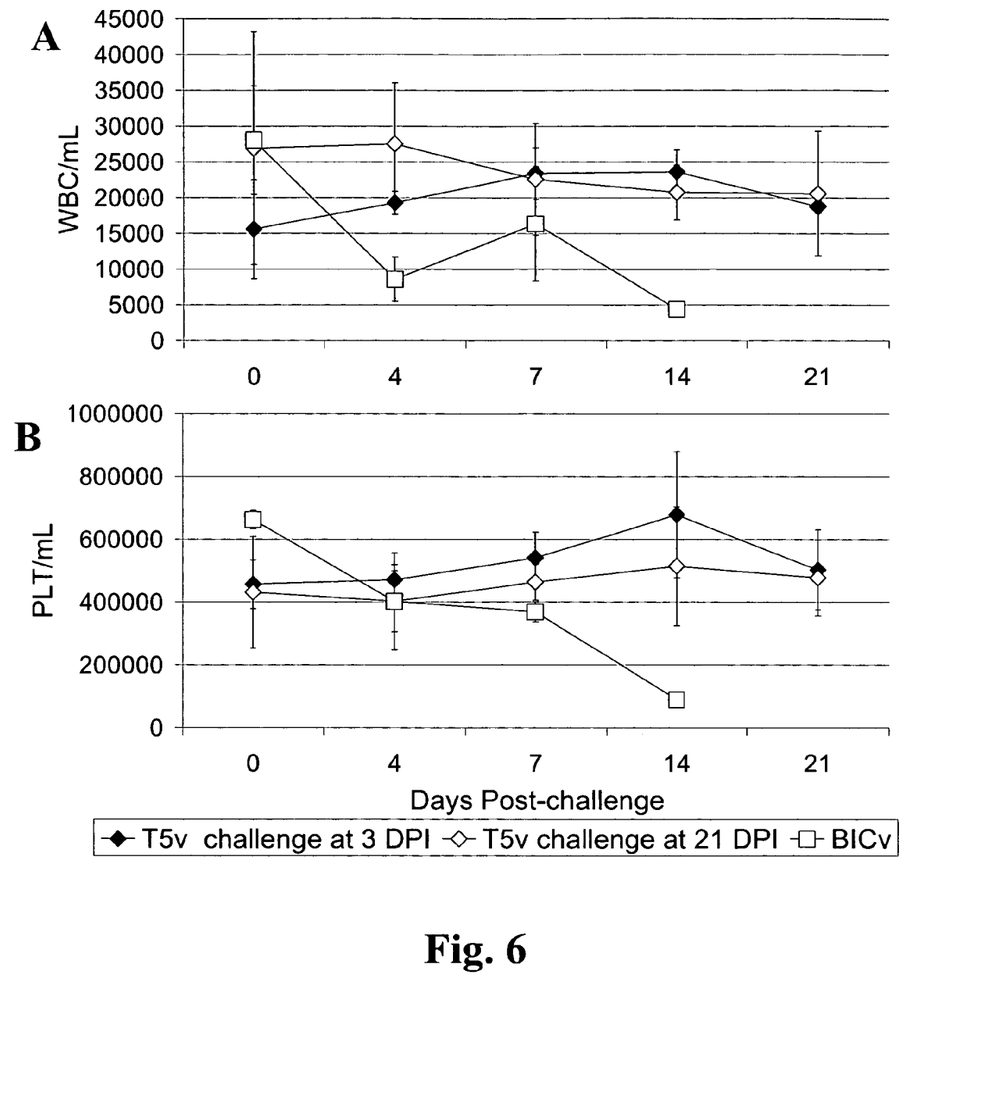
FIGS. 6A-B show peripheral white blood cell (FIG. 6A) and platelet counts (FIG. 6B) in pigs mock vaccinated or vaccinated with T5v and challenged at 3 or 21 DPI with BICv. Values for control, mock vaccinated, and challenged animals are represented with filled squares. Counts are expressed as numbers/ml and represent the mean of four individuals with error bars indicating standard error.

The ability of T5v to induce protection against BICv challenge was evaluated. Swine vaccinated with T5v were challenged at 3 or 21 DPI with $10^5$ TCID$_{50}$ of pathogenic BICv. Mock vaccinated control pigs receiving no T5v developed anorexia, depression, and fever by 4 days post challenge (DPC) with BICv, developed a marked reduction of circulating leukocytes and platelets by day 7 DPC, and had died or were moribund and euthanized by 12 DPC (Table 4 and FIG. 6).

TABLE 4

Swine survival and fever response of T5-infected animals following challenge with BICv.

| Challenge DPI[1] | Survivors/ Total | Mean time To Death Days (SD) | Mean time Fever Onset Days (SD) | Mean time Duration Fever Days (SD) | Average Max. Daily Temp. (SD) |
|---|---|---|---|---|---|
| 3 | 4/4 | — | 4 (0.8)[2] | 1 (0.0) | 103.1 (0.6) |
| 21 | 4/4 | — | — | — | 102.9 (0.3) |
| Control[3] | 0/2 | 12 (0.0) | 4 (0.0) | 5 (0.7) | 105.9 (0.7) |

[1]Days post-infection with T5
[2]Two out of 4 animals presented fever
[3]Control: animals were mock vaccinated Notably, T5v induced by 3 DPI complete protection against BICv-induced clinical disease. All pigs survived infection and remained clinically normal, with only two animals presenting with a transient fever at 4 DPC (Table 4) and without significant changes in their hematological values (FIG. 6). Similarly, pigs challenged at 21 days post T5v infection remained clinically normal (Table 4).

Viremia and virus shedding of BICv challenge virus as specifically detected with mAb WH303 was also examined at 4, 6, 8, 14 and 21 DPC (data not shown). As expected in mock-vaccinated control animals, BICv viremia was observed by 5 DPC, with virus titers remaining high ($10^6$ TCID$_{50}$/ml by 8 DPC) until death, and BICv was titrated from nasal swabs and tonsil scrapings by 4 DPC, reaching titers of $10^4$-$10^5$ TCID$_{50}$/ml) by 8 DPC. In contrast, BICv was absent in all clinical samples (blood, nasal swabs, or tonsil scrapings) from T5v-vaccinated swine following challenge. These results indicate that T5v is able to rapidly induce complete protection against lethal CSFV challenge, that T5v-immune swine demonstrate no detectable viremia or shedding from challenge virus.

Thus, T5v is able to induce in experimentally vaccinated animals complete protection against both the presence of clinical disease and the replication of the challenge virus when challenged with the virulent parental virus Brescia either at 3 or 28 days after T5 vaccination.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A recombinant classical swine fever virus (CSFV) comprising DNA encoding a mutated CSFV E2 glycoprotein, wherein amino acids 829-837 of said E2 glycoprotein are substituted with the sequence TSFNMDTLR (SEQ ID NO:6), a modification resulting in attenuation of CSFV.

2. A recombinant classical swine fever virus (CSFV) comprising DNA encoding a mutated CSFV E2 glycoprotein, wherein amino acids 829-837 of said E2 glycoprotein of the strain Brescia are substituted with the sequence TSFNMDTLA (SEQ ID NO:7) and the modification consisting of said TSFNMDTLA results in attenuation of CSFV.

3. A classical swine fever vaccine comprising a recombinant rationally designed live attenuated classical swine fever virus according to claim 1.

4. A classical swine fever vaccine comprising a recombinant rationally designed live attenuated classical swine fever virus according to claim 2.

5. A strategy for producing an attenuated recombinant classical swine fever virus according to claim 1 or claim 2 comprising:
   (a) identifying a virulence determinant in the highly pathogenic strain Brescia;
   (b) identifying a homologous virulence determinant in a related virus, said virus not pathogenic in swine;
   (c) progressively and sequentially mutating the DNA encoding said virulence determinant, whereby progressive mutations in said DNA result in a change of amino acids characteristic of the CSFV virulence determinant to amino acids characteristic of the homologous virulence determinant; and
   (d) achieving attenuation of CSFV.

6. A method of immunizing an animal against CSF, comprising administering to said animal, a vaccine comprising a recombinant classical swine fever virus according to any one of claims 1 and 2.

7. A method of protecting an animal against CSF, comprising administering to said animal an amount of the vaccine of any one of claims 3 and 4 effective to protect said animal from clinical CSF.

* * * * *